United States Patent [19]

Eaton

[11] 4,383,438
[45] May 17, 1983

[54] FOULING TEST APPARATUS

[75] Inventor: Paul E. Eaton, Cedar Hill, Mo.

[73] Assignee: Petrolite Corporation, St. Louis, Mo.

[21] Appl. No.: 269,178

[22] Filed: Jun. 2, 1981

[51] Int. Cl.³ ............................................ G01N 17/00
[52] U.S. Cl. ......................................... 73/61.2; 374/7
[58] Field of Search ...................... 73/7, 61.2; 422/53

[56] References Cited

U.S. PATENT DOCUMENTS 3,552,189  1/1971  Courvoisier et al. .
3,918,300  11/1975  Weisstuch et al. .
4,024,751  5/1977  Potrzebowski .

OTHER PUBLICATIONS

Taylor et al., "I. & E. C. Product Research and Development", vol. 6, No. 4, Dec. 1967, pp. 258–262.
Welder et al., "Dynamic Deposit Monitor–. . . ", Paper presented at the 36th Annular Meeting of the International Water Conference, Nov. 4–6, 1975.
Knudsen, "Apparatus and Techniques for Measurement of Fouling . . . ", Paper presented at the International Conference on Fouling of Heating Equipment, Aug. 13–17, 1979.
Fischer et al., "Chemical Engineering Progress", vol. 71, No. 7, Jul. 1975, pp. 66–72.
Hasson et al., "Desalination", vol. 5 (1968), pp. 107–119.
Klonowski et al., "Materials Performance", Aug. 1980, pp. 45–47.
Benson et al, "I. & E. C. Product Research and Development", vol. 1, No. 1, Mar. 1962, pp. 7–10.
Haluska, "Hydrocarbon Processing", Jul. 1976, pp. 153–156.
Steele et al., "Predictive Test Method for Coking and Fouling Tendency of Used Lubricating Oil", Technical Information Center, U.S. Department of Energy, May 1979, (12 pp.).

Primary Examiner—Herbert Goldstein
Attorney, Agent, or Firm—Sidney B. Ring; Hyman F. Glass; Leon Zitver

[57] ABSTRACT

A fouling test apparatus comprising a cylindrical pressure vessel, means for controlling the temperature of fluid contained in the vessel, cylindrical probe having a metallic surface concentric with the vessel walls and provided with a heater for such surface; stirrer in the form of a rotor open at at least one end and positioned between and concentric with the vessel walls and the probe, and sensor for measuring the temperature of the fluid contained in the vessel and the temperature of the probe surface. The probe simulates a heat exchanger surface exposed to a fouling liquid medium. Deposits accumulate on the heated surface in a similar fashion to an actual system and the parameters which affect fouling are all represented. The probe operates with a constant heat flux. As deposits accumulate, the surface temperature of the probe increases and is used as a measure of the deposit formation. The probe is maintained in a stationary position and the stirrer is not dependent on an electrical feed-through.

12 Claims, 1 Drawing Figure

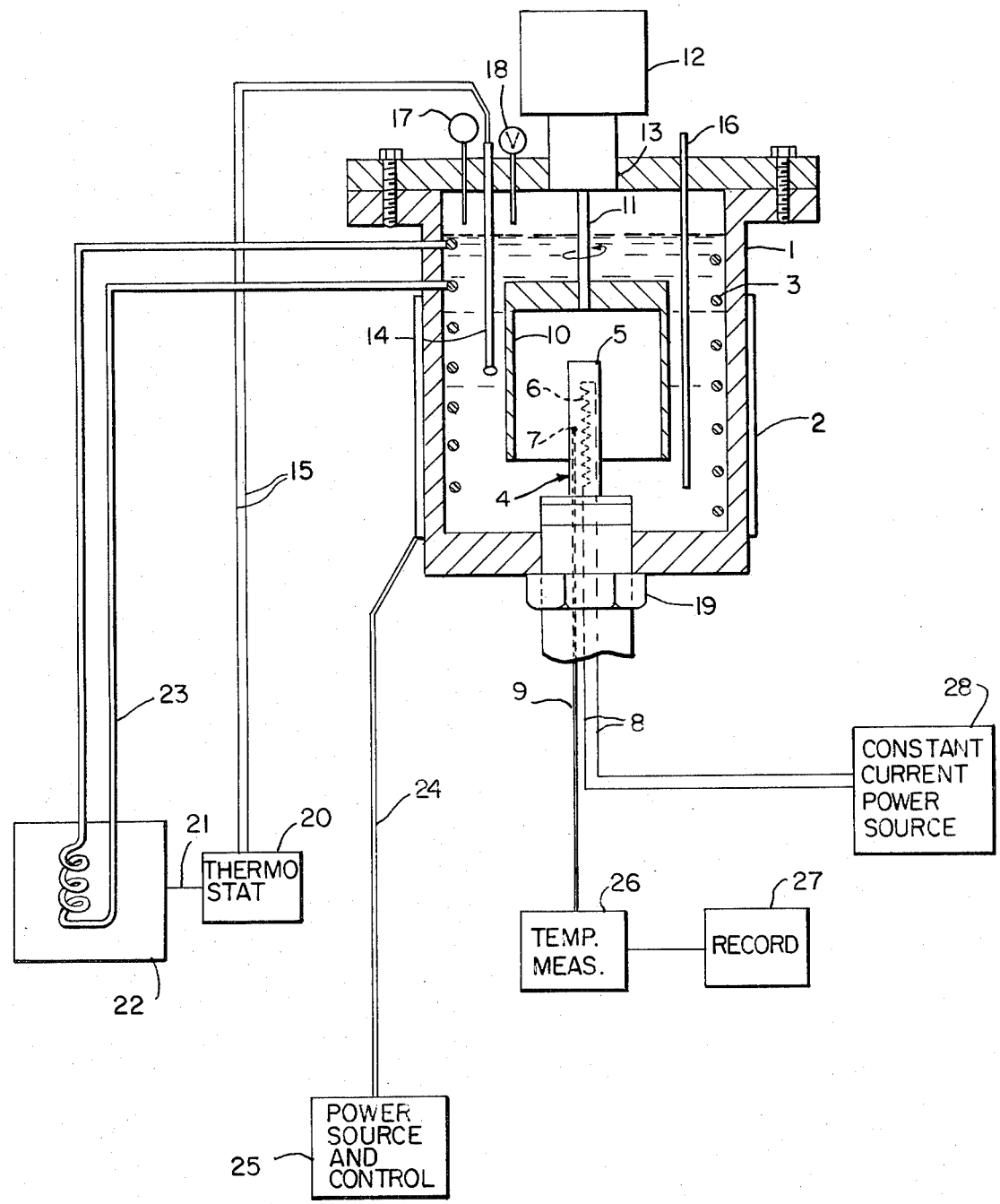

FOULING TEST APPARATUS

BACKGROUND OF THE INVENTION

This invention relates to apparatus and procedures for carrying out fouling tests in a laboratory environment. More particularly, the fouling test involved is one designed to simulate a heat exchanger surface such as a particular section of a heated exchanger tube exposed to a fouling liquid medium.

In designing apparatus and procedures of the type involved, the problem is to generate and measure in a laboratory environment a fouling deposit representative of that produced in the field. The information obtained by carrying out such fouling tests enables various antifoulant treatments to be evaluated as well as other factors which may mediate the fouling process.

The prior art has addressed the problem in a number of different ways, using types of apparatus and procedures which may be summarized as follows:

1. Pipe loops—These mainly involve procedures wherein very large quantities of oil are pumped through a heated pipe section of some sort and the foulant deposited on the pipe surface (either inner or outer, depending on which surface is heated) during the test is weighed. In addition to requiring large quantities of oil, very complex and expensive equipment, e.g. flowmeters, flow controller and pumps, is required. Moreover, because fouling severity depends upon the heat transfer coefficient, which is influenced by the flow and flow changes along the length of the pipe, the fouling is ill-defined and poorly reproduced. 2. Pilot scale heat exchangers—These involve procedures where, employing pilot scale heat exchangers, heat transfer coefficients are utilized as a measure of fouling. These suffer from the same disadvantages as pipe loops and, in addition, require very long times to establish a fouling condition. Moreover, the fouling cannot be quantified by measurement, since the heat transfer coefficient measures the net effect of all the tubes, which may be in varying conditions of cleanliness.

3. Autoclaves—These include autoclaves provided with either rotating heated cylinders or with stationary heated cylinders under stirred or flow through situations. The use of rotating heating cylinders is an effective way to generate fouling at well defined flow conditions, but requires expensive and hard to maintain rotating electrical feed throughs. Such rotating feed throughs may become hazardous when gaseous petroleum environments are involved. Stationary heated cylinders in stirred or flow through autoclaves are not capable of establishing a well defined and reproducible flow field.

4. Hot wire elements—In this procedure, a preheated oil stream contacts a hot metal wire, the temperature of the wire modeling a heat exchanger's hot wall temperature. However, in this procedure, the velocity effects on the deposit growth are not reproducible.

5. Filtration devices—In these procedures, oil is pumped through heated filters. Deposits build up, plugging the filters. However, there is no way to simulate the velocity effect in these procedures.

An object of the present invention is to provide a fouling test apparatus producing a well defined and reproducible flow field. A further object of the invention is to provide such apparatus having no rotating electrical feed-throughs. An additional object of the invention is to provide such apparatus wherein a signal representing fouling severity can be directly related to an actual physical measure of fouling, such as foulant thickness or weight. Yet another object of the invention is to provide such apparatus wherein small amounts of test fluid are required, in situ fouling monitoring is possible, a short time is required for determining fouling tendency, and specific fouling conditions may be maintained for long periods of time, thereby allowing detailed studies of these conditions. Other objects of the invention, including the provision of procedures for employing such apparatus, will become apparent from the following description and the appended drawing.

SUMMARY OF THE INVENTION

The above and other objects of the invention are achieved by providing a fouling test apparatus comprising a cylindrical pressure vessel; means for controlling the temperature of fluid contained in the vessel; stationary cylindrical probe means having a metallic surface, positioned in the vessel concentrically with its walls, the probe being provided with means for heating its surface; cylindrical stirring means in the form of a rotor open at at least its lower end, positioned in the vessel concentrically with its walls and between the probe means and the vessel walls; means for rotating the stirring means free of electrical feed-throughs; means for measuring the temperature of fluid contained in the vessel; and means for measuring the temperature of the probe surface.

The stirring means is preferably a cup shaped rotor powered by magnetic drive means. The temperature measuring means are preferably thermocouple means connected to monitoring means outside of the vessel. The means for controlling the temperature of fluid contained in the vessel may include both heating and cooling means and thermostat means. The heating means preferably include a heating jacket around the vessel and the cooling means preferably include a cooling coil within the vessel near its inner wall. The means for heating the surface of the probe preferably include an electrical heating element within the probe.

The invention also includes a fouling test procedure which comprises introducing the fluid to be tested into a pressure vessel having a stationary probe projecting into the body of the fluid, bringing the body of fluid to and maintaining it at a substantially constant elevated temperature, heating the probe by supplying a constant heat input to it, causing the body of fluid to circulate concentrically around the probe, and monitoring the temperature difference between the probe and the body of fluid over a period of time and/or measuring the amount of foulant deposited on the probe surface after a period of time.

BRIEF DESCRIPTION OF THE DRAWING

The drawing FIGURE shows a schmetic representation of a preferred embodiment of the fouling test apparatus of this invention.

DESCRIPTION OF SPECIFIC EMBODIMENT

The apparatus consists of a pressure vessel 1 provided with an outer heating jacket in the form of a band heater 2 and a cooling coil 3 adjacent to the inner wall of the vessel. Vessel 1 is equipped with an axially positioned stationary probe 4 secured to the vessel as by being fastened to the bottom thereof in a leakproof fashion by means of a swedge lock connector 19. The probe 4 includes a metallic housing 5 enclosing an electrical resistance heating element 6 and a thermocouple 7 in contact with the inner wall of housing 5. Electrical leads 8 and 9 extend from resistance heating element 6 and thermocouple 7, respectively, to the outside of vessel 1. A cylindrical stirring rotor 10 in the shape of an inverted cup is positioned in vessel 1 concentrically with and between probe 4 and the wall of vessel 1. Rotor 10 is attached to an axially positioned shaft 11, attached to a magnetic drive 13 secured to the top of vessel 1 and is caused to rotate around probe 4 by an electric motor 12 via the magnetic drive. Other means for rotating the rotor 10 may be substituted for the magnetic drive as long as it does not cause leakage from vessel 1 or involve rotating electrical feed-throughs. The magnetic drive is desirable because it provides a low torque and zero leak condition. A second thermocouple 14 extends into vessel 1, being preferably positioned between rotor 10 and the wall of the vessel. Electrical leads 15 extend from thermocouple 14 outside of vessel 1. A gas sparging tube 16 extends from outside the vessel 1 to the lower portion thereof. The vessel 1 is also provided with a pressure gauge 17 and a pressure relief device, such as a spring loaded valve 18.

Electrical leads 15 on the outside of vessel 1 connect with thermostat 20, which maintains the oil in vessel 1 at a substantially constant predetermined temperature by means of an interconnection 21 to cooling bath 22 and conventional means, not shown, for regulating the temperature and/or flow of coolant circulating through cooling coil 3 and conduit loop 23. Band heater 2 is connected via electrical leads 24 to power source and control means 25. Electrical leads 9 on the outside of vessel 1 connect with temperature gauge 26, which is preferably connected to a temperature recording device 27. Electrical leads 8 on the outside of vessel 1 connect with a constant current power source 28.

The above described apparatus is employed in fouling tests as follows, the fouling media tested being typically a hydrocarbon liquid, referred to hereinafter as an oil:

Before each run the surface of the probe 5 is sandblasted to remove any corrosion product or remaining deposits from previous runs. The probe is then washed with methanol, xylene, and acetone. The oil of interest is maintained in an air free container. Immediately prior to use a 700 ml sample is withdrawn, contaminants added (acid, caustic, inhibitor, etc.), and sheared in a high intensity mixer for two minutes, under gas atmosphere, e.g., air or nitrogen. The treated oil is then introduced into the pressure vessel 1 and gas sparged 15 minutes. The vessel is sealed and pressurized to 150 psi. The oil temperature is allowed to reach equilibrium and is then maintained by thermostat 20 and associated means at within ±5° F. of the desired predetermined temperature. When the oil temperature approaches equilibrium, power is applied to the heating element 6 of the probe. This results in a temperature difference between the probe and the oil which is continuously monitored with time. As deposit accumulates the probe temperature increases. The probe temperature changes only with accumulated deposit, because all other factors are maintained essentially constant. The probe operates with a constant current applied, which produces a constant heat input condition.

The test time depends on the fouling severity and may typically vary between 2 and 48 hours. Most tests are conducted for an 18 hour period. At the end of a test the oil is removed and the probe allowed to drain before removal. The probe is then photographed with whatever deposit has accumulated. The deposit is then removed and weighed. Fouling severity is determined by observing the change in probe-oil temperature difference with time (fouling curve) and also by observing the total weight accumulated during the run.

The measurement theory of the test is as follows: Heat is transferred from the clean cylinder to the cooler oil according to Fourier's Equation:

$$Q_c = U_c A_c \Delta T_c \text{ heat flux with probe clean where } A_c \text{ is the clean heat transfer area, and} \tag{1}$$

$$\Delta T_c = (T_{probe} - T_{oil})_{clean} \tag{2}$$

$$1/U_c = 1/h, \text{ where h is the convective heat transfer coefficient} \tag{3}$$

$$h = f_1(R_e, P_r) \tag{4}$$

$$P_r = f_2 \text{ (heat capacity, viscosity, thermal conductivity)} \tag{5}$$

$$R_e = f_3 \text{ (density, velocity, geometry, viscosity)} \tag{6}$$

As the deposit accumulates, it acts as a resistance to heat transfer, and Fourier's Equation becomes:

$$Q_d = U_d A_d \Delta T_d = \text{heat flux with probe dirty} \tag{7}$$

$$\Delta T_d = (T_{probe} - T_{oil})_{dirty} \tag{8}$$

$$1/U_d = 1/h + X/K \tag{9}$$

$$X = \text{deposit thickness} \tag{10}$$

$$K = \text{deposit thermal conductivity} \tag{11}$$

$$f = \text{fouling factor} = X/K \tag{12}$$

The fouling factor is defined as X/K or the fouling thickness divided by the deposit thermal conductivity. The fouling factor is expressible in terms of thermal parameters, which are measured during the test, by manipulation of equations 1, 3, 7, 9, and 12. Equations 3, 9, and 12 lead to:

$$1/U_d - 1/U_c = f \tag{13}$$

Substituting for $U_d$ and $U_c$ from equations (1) and (7):

$$f = A_d \Delta T_d / Q_d - A_c \Delta T_c / Q_c \tag{14}$$

For the purpose of simplicity the following conditions are assumed to apply.
1. Fluid properties remain essentially constant (i.e. oil thermal conductivity, viscosity, density, and heat capacity).
2. There is no physical change of state (i.e. no boiling).
3. Convective heat transfer coefficient (h) remains constant (i.e. fluid velocity close to the surface is constant).
4. Heat flux is constant throughout the test. ($Q_c = Q_d$)
5. The heat transfer area remains essentially constant throughout the fouling process. ($A_c = A_d$)
6. The thermal and physical properties of the deposit remain constant throughout the test.

Equation 14 along with assumptions 1 to 6 lead to:

$$f = (A/Q)(\Delta T_d - \Delta T_c) \tag{15}$$

Substituting equation 12 into equation 15;

$$X/K = (A/Q)(\Delta T_d - \Delta T_c) \quad (16)$$

The fouling thickness X is expressible in terms of deposit weight, density and area according to:

$$X = \text{weight}/(\text{density})(\text{area}) \quad (17)$$

Solving for $\Delta T$ change from equation 16:

$$\Delta T \text{ change} = Q/K\rho A^2(\text{weight}) \rightarrow \text{weight} = K\rho A^2/Q \Delta T \text{ change} \quad (18)$$

A plot of the experimental data ($\Delta T_d - \Delta T_c$) vs. weight should therefore yield a straight line having the slope $K\rho A^2/Q$. The nearness to linearity could be used as a check on the validity of assumptions 1 to 6, and also as a means for determining the unknown values of deposit density and thermal conductivity.

The results of over 100 experiments carried out on five separate oils were plotted and subjected to statistical analysis. A straight line drawn through a plot of the data ($\Delta T_d - \Delta T_c$) vs. deposit weight using the calculated mean slope of 0.00154 grams/°F. gave a correlation coefficient of 0.936. The standard deviation showed that 67% of the data fell within 0.00154±0.000739 grams/$\Delta T$ change. These results indicate that the relation between deposit weight and fouling factor, as above defined, is quite good and that therefore the assumptions as to 1 to 6, above listed, are reasonable.

It will be seen from the above discussion that the apparatus and procedure of this invention may be used to obtain two different measurements, both representative of the fouling severity. The first utilizes the net weight of the deposit accumulated during a given time. This is a simple and direct measure of the resulting deposit. However, some information is lost because in situ measurements are not possible. For example, it is not known exactly how the deposit formed with time during the test.

The second measurement method makes up for some disadvantages of the first. The fouling factor is continuously measured with time. Indirectly the deposit is monitored by its influence on heat transfer. The primary benefit of this approach is that it does provide information on how the deposit forms throughout the course of the experiment. The resulting plot of fouling factor vs. time is called a fouling curve. In general the characteristic of fouling curves obtained thus far is a dead time followed by a rapid increase in fouling, followed by a leveling off. The dead time is interpreted as a period of time during which little or no fouling occurs. Presumably, this phenomenon occurs because surface sites must be filled or a given species must be produced at sufficient levels before fouling can proceed.

The rapid increase in fouling is interpreted as the actual rate of the fouling reaction. It is the maximum rate of fouling which can occur within the constraints of the test (i.e. velocity, temperature, concentration of foulants, etc.).

The leveling off region of the fouling curve is labeled asymptotic fouling. It can have three interpretations: (1) The concentration of foulants has been depleted, thereby halting the fouling reaction. (2) The accumulation is exactly balanced by the removal of deposits. (3) The deposit morphology is changed during the test. The fouling reaction could be stimulated by iron appearing in a corrosion product. As deposits build, iron is diluted with coke accumulation.

Clearly, a chemical treatment to reduce fouling would be effective if it influenced any of these three key fouling curve variables. However, information as to the mechanism of the fouling could also be obtained depending on which variable was affected.

It will be seen that the apparatus of the present invention well simulates a heat exchanger surface exposed to a fouling liquid medium. Deposits accumulate on the heated probe surface in a similar fashion to an actual heat exchange system, and the parameters which affect fouling in the real system are all represented. The fluid velocity is simulated by rotating a hollow cylinder around the heat probe. In the apparatus above described, rotor angular velocities of up to 1000 r.p.m. are achievable; a probe surface temperature of 1200° F. can be reached; the oil temperature is controllable, within ±5° F., to 500° F.; and the working pressure within the vessel may be as high as 500 psi.

Although the invention has been described in detail by way of a preferred embodiment, it will be understood that such description, including the above described working parameters, is by way of illustration only, and it is contemplated that modifications and variations may be made by those skilled in the are without departing from the spirit of the invention.

I claim:
1. Fouling test apparatus comprising:
    (a) a cylindrical pressure vessel;
    (b) means for controlling the temperature of fluid contained in said pressure vessel;
    (c) stationary cylindrical probe means having a metallic surface, positioned in said pressure vessel concentrically with the walls thereof, said probe means including means for heating the probe surface;
    (d) cylindrical rotary stirring means open at at least its lower end, positioned in said pressure vessel concentrically with the walls thereof and intermediate said probe means and said pressure vessel walls;
    (e) means for rotating said stirring means free of electrical feed-throughs;
    (f) means for measuring the temperature of fluid contained in said pressure vessel; and
    (g) means for measuring the temperature of the surface of said cylindrical probe means.
2. The apparatus of claim 1 wherein said stirring means is powered by magnetic drive means.
3. The apparatus of claim 1 wherein said stirring means is cup shaped.
4. The apparatus of claim 1 wherein said temperature measuring means (f) and/or (g) are thermocouple means connected to monitoring means outside said pressure vessel.
5. The apparatus of claim 4 wherein said monitoring means include means for displaying and/or recording the difference in the temperatures sensed by measuring means (f) and (g).
6. The apparatus of claim 1 wherein said means for controlling the temperature of fluid contained in said pressure vessel comprises heating means/or cooling means.
7. The apparatus of claim 6 wherein said means for controlling the temperature of fluid contained in said pressure vessel further includes thermostat means.

8. The apparatus of claim 6 wherein said heating means comprises a heating jacket around said pressure vessel and said cooling means comprises a cooling coil positioned within said vessel adjacent to the inner wall thereof.

9. The apparatus of claim 1 including also gas sparging means.

10. The apparatus of claim 1 wherein said probe means includes an electrical heating element within a cylindrical metallic housing.

11. A fouling test procedure comprising introducing the fluid to be tested into a pressure vessel having a stationary probe projecting into the body of said fluid, maintaining said body of fluid within said pressure vessel bringing said body of fluid to and maintaining it at a substantially constant elevated temperature, heating said probe by supplying a constant heat input thereto, causing said body of fluid to circulate concentrically around said probe, and monitoring the temperature difference between said probe and said body of fluid over a period of time.

12. A fouling test procedure comprising introducing the fluid to be tested into a pressure vessel having a stationary probe projecting into the body of said fluid, maintaining said body of fluid within said pressure vessel bringing said body of fluid to and maintaining it at a substantially constant elevated temperature, heating said probe by supplying a constant heat input thereto, causing said body of fluid to circulate concentrically around said probe, and measuring the amount of foulant deposited on the probe surface after a period of time.

* * * * *